United States Patent [19]

Acevedo et al.

[11] 4,228,127

[45] * Oct. 14, 1980

[54] KIT FOR DETECTING HUMAN CHORIONIC GONADOTROPIN

[75] Inventors: Hernan F. Acevedo, Allison Park; Malcolm Slifkin, Pittsburgh; Milton H. Dalbow, Springdale, all of Pa.

[73] Assignee: International Radioimmune Systems, Inc., Howell, Mich.

[ * ] Notice: The portion of the term of this patent subsequent to Mar. 13, 1996, has been disclaimed.

[21] Appl. No.: 949,330

[22] Filed: Oct. 6, 1978

Related U.S. Application Data

[62] Division of Ser. No. 677,992, Apr. 19, 1976, Pat. No. 4,144,031.

[51] Int. Cl.$^2$ .................... G01N 33/16; G01N 31/14
[52] U.S. Cl. .................... 422/61; 23/230 B; 23/915; 424/8; 424/12; 435/4; 435/28
[58] Field of Search .................... 23/230 B; 424/8, 12; 195/103.5 A; 422/61; 252/408; 435/4, 28

[56] References Cited

U.S. PATENT DOCUMENTS

| | | | |
|---|---|---|---|
| 3,654,090 | 4/1972 | Schuurs | 195/103.5 A |
| 3,697,638 | 10/1972 | Hansen | 424/12 X |
| 3,720,760 | 3/1973 | Bennich | 23/230 B X |
| 3,789,116 | 1/1974 | Kay | 424/12 X |
| 3,868,219 | 2/1975 | Hurenkamp | 424/12 X |
| 3,873,683 | 3/1975 | Fishbein | 424/12 |
| 3,901,654 | 8/1975 | Gross | 23/230 B |
| 3,935,074 | 1/1976 | Rubenstein | 195/103.5 A |
| 3,992,514 | 11/1976 | Donini | 23/230 B X |

OTHER PUBLICATIONS

Chemical Abstracts, 81:985x (1974).
Chemical Abstracts, 80: 2073b (1974).
J. J. Munoz, Anal. Chem., 31 (6), 981-985 (1959).

*Primary Examiner*—Sidney Marantz
*Attorney, Agent, or Firm*—Cullen, Sloman, Cantor, Grauer, Scott & Rutherford

[57] ABSTRACT

A diagnostic cell test and kit for detecting human chorionic gonadotropin as evidence of cancer. The subject's cells undergoing examination are contacted with antiserum specific to the beta-subunit of human chorionic gonadotropin, the antiserum having been raised in a host animal. The treated cells are divided into two portions. The portions are treated with antiserum to the gamma globulin of the host animal. The antiserum to the gamma globulin used in treating the first portion is conjugated to fluorescin, and the antiserum used in contacting the second portion is conjugated to peroxidase. A positive test for cancer is concluded only when both tests on the two portions of the cells are positive.

1 Claim, 6 Drawing Figures

KIT FOR DETECTING HUMAN CHORIONIC GONADOTROPIN

This is a division of application Ser. No. 677,992, filed Apr. 19, 1976, now U.S. Pat. No. 4,144,031.

FIELD OF THE INVENTION

Generally, the present invention relates to a diagnostic procedure and clinical test kit for determining the presence or absence of human chorionic gonadotropin hormone, a glycoprotein, in a cell specimen and thereby the absence of malignant neoplastic cells.

The reason why a mother is able to accept her fetus as an allograph when a large percentage of the potential antigenic sites of the fetus are different from those of the mother, has long been a mystery. It is known that the fetal trophoblast engrafts itself on the maternal endometrium while exposed to immunocompetent maternal lymphocytes. It has now been suggested that human chorionic gonadotropin is a trophoblastic surface antigen which blocks the action of the maternal lymphocytes, Adcock, et al, Science, Vo. 181, 845–847 (1973).

Human chorionic gonadotropin (hCG) has been detected very early in gestation (seven days) and is now used as a diagnostic test for pregnancy. As stated, this hormone is a glycoprotein and, like other glycoprotein hormones including follicle-stimulating hormone (hFSH), luteinizing hormone (hLH) and thyrotropin, it consists of two non-covalently linked subunits, including alpha and beta. In contrast to the alpha-subunits, the amino acid composition of the beta subunit of hCG differs substantially from the other glycoproteins.

The larger beta-subunit of hCG is the hormone-specific unit. A sizeable portion (30 percent) of the hCG molecule is carbohydrate and the sialic acid moiety is essential for some of its biological activities. The concentration of hCG in both maternal blood and urine rises to a maximum during the first trimester of pregnancy and declines thereafter to a low level during the latter portion of pregnancy. Most pregnancy tests are based upon this peak concentration or titer of hCG during the first trimester.

It has also been determined that certain malignant tumors, test positive for hCG, and hCG has been found in the serum of patients having malignant tumors. For example, in a recent study, malignant cells were tested for hCG using the indirect peroxidase-labeled antibody technique specific for the beta subunit of hCG. Of the known malignant tumors tested, 10 tested positive and 5 tests were considered equivocal. Because the alpha subunit of hCG and hLH are virtually identical, the antiserum to the beta subunit of hCG was chosen which shares less homology with hLH, Vaitukaitis, et al, Am. J. Obstet. Gynecol., Vol. 113, No. 6, 751–758 (1972).

Similarly, serum tests for hCG of patients with known malignant tumors have been inconclusive. For example in one recent study, 40 percent of all men with malignant tumors tested positive for hCG and up to 90 percent were positive among ovarian and testicular tumors, Barber et al, J. St. Barnabas Med. Ctr., Symposium August 1975. The only conclusion therefore that may be drawn from the prior art publications is that the detection of hCG in a nonpregnant woman or man "implies that a hCG secreting tumor is present", Barber et al, supra.

A common chemical or biological denominator for cancer which may provide a simple diagnostic test has long been sought but never found. The present clinical procedure and diagnostic test kit provides the solution.

SUMMARY OF THE INVENTION

It has now been established by the combination of serially performed double-antibody tests of this invention that all malignant neoplastic cells synthesize human chorionic gonadotropin. Contrary to the teaching of the prior art, therefore, the absence of hCG in a cell specimen establishes the absence of cancer. The diagnostic cell test of this invention first includes treating the cells to be tested with antiserum specific to the beta-subunit of hCG raised in a host animal, commonly a rabbit. Different samples of the treated cells are then serially treated with antiserum specific to the gamma globulin of the host animal which was used to raise the specific antiserum to the beta-subunit of hCG; one labeled or conjugated to flurorescein and the second conjugated to peroxidase. An example of the second antibody is sheep anti-rabbit gamma globulin G.

The indirect fluorescein-labeled antibody test is considered positive where green-apple fluorescence is found under a fluorescent light microscope. Where no fluorescence is seen, the test is negative. The indirect peroxidase-labeled antibody test is considered positive where peroxidase staining of the cells is found by viewing the cells in a microscope. Where no peroxidase staining is found, the test is negative. Only where both indirect labeled antibody tests are positive is the diagnostic cell test of this invention considered positive for human chorionic gonadotropin. Where both cell tests are negative or where one indirect test is positive and the other is negative, the diagnostic cell test is negative and the cell sample does not include malignant neoplastic cells.

DETAILED DESCRIPTION

Figure 1:

As stated, a number of investigators have recognized that hCG is present in certain neoplasms, particularly ovarian and testicular tumors, as determined by cell tests, and that certain malignant tumors secrete hCG, as determined by serum tests. Human chorionic gonadotropin is normally a product of the trophoblast and its presnce in non-pregnant women and men has suggested to certain investigators the presence of a "human chorionic gonadotropin secreting tumor", Barber et al, supra. The role of hCG in regard to malignant tumors has not been fully understood, however it has been suggested that there is a parallelism between the syncytiotrophoblast and tumors, Naughton et al, supra.

It is believed that the failure of the prior art to detect hCG in certain malignant tumors results from a failure of the testing procedure utilized. Human Chorinic Gonadotropin has now been identified in cancer cells from a wide variety of in vitro (tissue culture) and in vivo (experimental animal) systems using two highly specific and sensitive immunohistochemical methods. It can now be said that all cancer cells synthesize hCG. Further, tests have shown that the survival potential of the cancer cell as a homograft may be related to the concentration of the hormone or prohormone at the level of the cell membrane.

Using the combination of the highly specific indirect peroxidase-labelled and fluorescein-labelled antibody tests, the present inventors have identified and localized the beta-subunit of hCG in cancer cells grown in tissue culture, tissue imprints on glass slides as well as in sections of a group of experimental malignant neoplasms. With these highly specific and sensitive techniques, the beta-subunit of hCG was found to be present in a wide variety of cultured neoplastic cells, including HeLa, Hep-2 and P-815-X2. A large number of normal cultured cells from different species were used as controls and all normal cells tested negative for the presence of hCG. The hCG hormone was also identified in the sections of the primary as in the metastases of experimental malignant tumors, such as P-815-X2, Rauscher's Leukemia, Lewis lung carcinoma, etc., as described below:

The identification of the beta-subunit of hCG in all of these neoplastic cells proves that the embryonal hormone is synthesized by the tumor cell and appears to be a common product of every cell with oncogenic properties, even non-invasive malignant cells such as HeLa and Hep-2. The localization of a high concentration of hCG at the level of the plasma membrane in the infectious cells appears to explain the failure of the immune mechanism of the host due to the immunosuppressive activity of the hormone. The correlation between the concentration of hCG and the tumorginicity of the cell will be described more fully hereinbelow. Further, the production of hCG by the cancer cell appears to explain the lack of feedback control of the de novo synthesis of cholesterol due to continuous stimulation of the cholesterogenisis. This endogenous nonesterified cholesterol, since it is one of the main constituents of the cell and organelle membranes, is essential for growth and multiplication of cells.

The presence of the hormone in such a heterogeneous group of neoplastic cells can only be explained by the depression or inhibition of the genetic control and confirms that differentiated cells do carry information for all potential cell phenotypes.

While all cancer cells tested positive for the presence of hCG, there was an evident variation in the intensity of the immunostaining among the three types of cells tested, including a difference in the concentration of the glycoprotein. The HeLa cell displayed a discrete immunostaining in the cell membrane. Higher magnification revealed regular size peroxidase granules in the intermittent zones of the microvilli. The HeLa cell is considered a noninvasive malignant cell. In contrast, the highly tumorigenic or infective malignant cells displayed dense zones of electron-opaque reactive products, which was demonstrated with mastocytoma cells. Since the mastocytoma cell was obtained from ascites fluid, as described below, it can be considered a metastatic cell. On the other hand, the cells from the sections of the mammary adenocarcinoma represent a primary malignant neoplasm with metastatic potential. The correlation of the electron microscope findings with the physiologic characteristics of the cancer cells is notable and strongly supports the proposition that tumorigenicity is related to the concentration of the protein hormone (hCG) in the plasma membrane due to the immunological inertness of the compound.

It can now be said that human chorionic gonadotropin is a common denominator of every cell with oncogenic properties. The embryonal hormone or prohormone hCG is synthesized by the tumor cell. The identification of beta hCG in such a heterogeneous group of malignant cells proves (1) that this unique trophoblastic hormone is synthesized de novo by the cancer cell, and (2) that its existence can only be explained by an expression of the information which opens the mechanism(s) for its biosynthesis, either by a derepression or an activation of the genetic control. It can now be established that the absence of hCG in a cell culture or cell mass establishes the absence of cancer. The diagnostic cell tests and kit which establishes the absence of human chorionic gonadotropin will now be described in detail.

The constituents of the diagnostic test kit are as follows; (1) antiserum specific to the beta-subunit of hCG, having been raised in a host animal, (2) antiserum to the gamma globulin of said host animal conjugated to fluorescein, (3) antiserum to the gamma globulin of said host animal conjugated to peroxidase, and (4) controls. Antiserum specific to the beta-subunit of hCG is available commercially from various sources, including International Radioimmune Systems, Inc., Howell, Mich., Serono Laboratories, Inc., Boston, Mass., etc. Generally, this first antiserum is produced as follows.

Human chorionic gonadotropin is obtained and purified from human placentae. The beta-subunit is separated and purified as described by others; Vaitukaitis et al, J. Clin. Endocrinol. 33:98 (1971). The purified beta-subunit of hCG is then serially injected into a host animal, commonly rabbits, raising the antibody in the host animal. The animal is bled, and the antiserum is extracted and purified as described in Naughton et al, supra.

The fluorescein and peroxidase labelled second antibody may also be obtained commercially from Cappel Laboratories, Philadelphia, Pa. and International Radioimmune Systems, Inc. Where the first host animal is a rabbit, anti-rabbit gamma globulin is used. For example, rabbit immunogamma globulin G (IgG) is injected into a second host animal, such as a sheet or goat. The second host animal is then bled and the anti-rabbit gamma globulin is extracted, purified and labeled by conjugation with peroxidase and fluorescein. The methods of conjugating peroxidase and fluorescein anti-rabbit gamma globulin is described in Methods In Enzymology, Vol. 37, Watkins, Academic Press, p.256 (1975).

As described, the indirect peroxidase-labelled and fluorescein-labelled antibody tests for human chorionic gonadotropin are performed serially. Either test may be performed first, however, it is the combination of these tests which has established hCG as a common denominator of every cell with oncogenic properties. Further, the absence of hCG establishes the absence of cancer in the cells tested.

First, the tissue or cells to be tested must be prepared. In a typical test, cryostat sections of tissue are prepared on microscope slides. The sections are four microns thick, unfixed and air dried. The inventors have also discovered that slides may be prepared by touch smear impressions, wherein microscope slides are touched or impressed against the cell mass to be tested and air dried. Tissue cultures have also been investigated, which are placed on glass coverslips and air dried.

In each of the tests, rabbit anti-beta hCG was utilized. Each vial is reconstituted with the appropriate volume of phosphate buffered saline, pH 7.0, 0.01 M, as required. Goat or sheet anti-rabbit immunoagamma globulin G (IgG), conjugated to fluorescein is utilized in one of the tests as described. The following description will be directed to the indirect fluorescein-labelled antibody test. Each vial of the fluorescein-labelled goat anti-rabbit IgG is reconstituted with distilled water as required or as suggested by the supplier.

As described, at least two negative controls have been utilized in the present test. The first control is normal cells or cell cultures. These normal controls include non-malignant tumors and tissue cultures from normal subjects. For example, in one series of tests, human tissue cultures were used from an adult heart, adult liver, adult skin and muscle, adult cornea, diploid fibroblasts, from embryonic lung, embryonic kidney, adult prostatic hypertrophy and Rhesus monkey kidney tissue cultures.

The second controlled utilized in the present tests is a negative control antisera; for example, rabbit, anti-horse gamma globulin. Each vial is reconstituted with the appropriate volume of phosphate buffered saline as described above, pH 7.0, 0.1 M, as required. The test also requires a moist ambient temperature incubator and an ultraviolet microscope with primary and secondary filters (530 mu) for examination of immunofluorescence. The mounting media is preferably 95% glycerin in phosphate buffered saline (PBS).

A suitable procedure is then as follows. Remove the cell sample from the freezer (minus 20 degrees C.) if previously stored or utilize immediately after fixation as described above, before freezing. Place the slides on a flat, horizontal surface in the moist ambient temperature chamber and apply one drop (0.05 ml) of appropriately diluted antiserum specific to the beta-subunit of hCG. As described, it is preferable to simultaneously run a negative control on a similar substrate with a non-specific antiserum, such as rabbit anti-horse serum. The slides are then incubated in a moist ambient temperature chamber for thirty minutes. Gently rinse the excess antisera from the slides with PBS using a pipette. Then, wash the slides in PBS for ten minutes with gentle agitation, using Coplin jars or a large volume staining dish. Drain the slides briefly and blot or shake the excess fluid from around the tissue. Do not permit the tissue to dry at this point. Then, place the slides on a flat horizontal surface in the moist ambient temperature chamber, as described above, and add one drop of reconstituted fluorescein-labelled anti-rabbit IgG. Care must be taken to completely cover each substrate. The slides should then be incubated again for thirty minutes in the moist ambient temperature chamber. Then, rinse and wash the slides in PBS as by utilizing a pipette. Finally, apply a drop of mounting media and coverslip. The slides are now ready for examination.

Where fluorescein is used as the label, the slides are examined with an ultraviolet microscope with proper filters to permit the 530 mu light to pass through the tissue. The fluorescein stain, if present, will show as an apple-green fluorescence at the site of the beta hCG foci.

The indirect peroxidase-labelled antibody test utilizes the antisera described above in regard to the fluorescein-labelled antibody test. Further, a peroxidase stain is utilized as described below. One suitable peroxidase stain is 3,3'diaminodenzidine-tetra HCL (DAB). 3.5 mg DAB is dissolved in 10 ml phosphate buffered saline (PBS) as described above. Then, add 0.015 ml 30 percent $H_2O_2$. An alternate peroxidase stain is 3,3'diaminodenzidine (DAB). 7 mg DAB is dissolved in 10 PBS to which 0.01 ml of 30 percent $H_2O_2$ is added. This peroxidase stain is then filtered and utilized immediately. Also required for the peroxidase-labelled antibody test are absolute methanol, denatured ethanol and a counterstain. The counterstain is prepared by dissolving 0.2 gm of Light Green, a commercial preparation in 100 ml absolute methanol.

The tissue and cell preparation may be as described above in regard to the indirect fluorescein-labelled antibody test. The precedure is then as follows.

Add one drop (0.05 ml) of the antiserum specific for the beta-subunit of hCG to the slides containing the tissue or cells to be tested as described above. Again, good clinical procedure requires the use of a control, wherein negative serum control is added to a second slide. The slides are then incubated at room temperature in the moist atmosphere chamber for thirty minutes. Then, gently rinse excess antiserum from the slides with PBS using a pipette or the like. The slides are then placed in Coplin jars containing PBS using gentle agitation for ten minutes. Drain the slides briefly and shake excess fluid from around the tissue. Do not permit the tissue to dry. Then, add one drop of the second antiserum, which in this test is sheep or goat anti-rabbit IgG conjugated to peroxidase. Incubate the slide for thirty minutes in the moist atmosphere chamber, rinse and wash the slides with PBS as described above. Then, stain the cells with one of the peroxidase stains described above for ten minutes.

Following the staining with either DAB-HCL or DAB, wash the slides in PBS as described above. Then, rinse the slides for one minute in distilled water and dehydrate using two changes of reagenethanol (95 percent), one minute each change. The slides are then counterstained with Light Green for fifteen to twenty seconds using two to three slow dips. Destain the slides in absolute methanol for ten to fifteen seconds, again using two to three slow dips. Then, clear the slides wity xylene for one minute. Finally, with the xylene still on the cells, apply Permount and cover slip the slides. The slides are now ready for examination.

It will be understood that the preferred diagnostic test of this invention uses the double-antibody technique, the second antiserum providing a control against false positive tests. Further, the double antibody technique permits the use of two antisera controls; one nonspecific to hCG and the second nonspecific to the first antiserum, e.g. labeled rabbit anti-horse gamma globulin. In each case, the control should be labeled to avoid false positive tests. It may be possible however in certain applications to use a single antiserum technique where the first antiserum is labeled with peroxidase or fluorescein, reducing the time required for performing the tests.

As described, the slides are examined under a conventional light microscope for brown-black granules. Where the neoplastic cells are noninvasive or non-tumorigenic, such as the HeLa cell, intermittant or patchy staining occurs primarily at the plasma membrane or at the periphery of the cell. However, where the cell is invasive or tumorigenic, the stanining is more pronounced along the plasma membrane and intermittent zones of the microvilli.

Peroxidase as a label or marker offers several unique advantages. Because the histochemical reaction product is visable by both light and electron microscopes, peroxidase-labeled antibodies are applicable for localization of hCG at both the light and electron microscope levels. Horseradish peroxidase is a relatively small globular glycoprotein and, therefore, peroxidase-labeled immunoglobulin can penetrate through tissues almost as easily as unlabeled immunoglobulins. In addition, since the enzyme is not consumed in the histochemical reaction and many molecules of reaction product are deposited at the hCG sites, the method is extremely sensitive. The disadvantage of peroxidase as a label is that peroxidase may already be present in certain cells, including certain cancers, human spermatazoa, etc. Therefore, the indirect peroxidase-labeled antibody test may provide a "false" positive. Fluorescein as a label has the advantage that it is extremely visable under ultra-violet light, however fluroscence may also be present in certain cells. The fluorescein utilized in the present tests is fluorescein isothocyanate (FITC) which is a flurochrome. Each of these tests have been utilized in detecting various hormones, however, such tests have been inconclusive or equivocal in detecting neoplastic cells. It is only the combination of the serially performed indirect peroxidase-labeled and fluorescein-labeled antibody tests which has been positive for all malignant neoplastic cells characterized as cancer.

Where both the indirect peroxidase-labeled and the fluorescein-labeled antibody tests are positive, human chorionic gonadotropin is present in the cells tested. Where both indirect tests are negative or where one test is positive and the other is negative, human chorionic gonadotropin is not present in the cells tested and cancer may be ruled out. This is an important distinction from the prior art, where negative or ambiguous tests were considered inconclusive. It must be rememberd that a positive test for hCG is not conclusive of cancer because trophoblast or sperm cells may have been tested. If the test is positive in a woman, a pregnancy test should be made.

Using the double antibody technique described, the beta-subunit of hCG has been identified and localized in experimental animal neoplasms and human cancer cells. The in vivo and in vitro experimental animal neoplasms are listed in Table I and the in vivo and in vitro human cancer and normal control cells are listed in Table II. The trophoblastic protein hCG has also been identified in all frozen sections and imprints from the primary as well as from the metastases of experimental malignant neoplasms such as Rausher leukemia. As described, a high intensity immunoreaction to beta hCG was characteristic of the most tumorigenic cells when compared to nontumorigenic cells such as HeLa, Hep-2, etc. Reagent controls, such as the elimination and substitution of the first antibody, and a number of normal adult and embryonic cultured cells used as cell controls, as described above, were always negative for the presence of the beta-subunit of human chorionic gonadotropin.

The identification of the beta-subunit of chorionic gonadotropin in such a heterogeneous group of malignant cells proves (1) that this unique trophoblastic hormone is synthsized de novo by the cancer cell, and (2) that its existance can only be explained by an expression of the information which opens the mechanism for its biosynthesis, either by a depression or an activation of the generic control. Most importantly, the utilization of the double antibody test establishes that the trophoblastic hormone hCG is a common denominator of every cell considered to be a cancer cell.

The following figures illustrate positive tests using the indirect peroxidase-labeled and fluroscein-labeled antibody test of this invention. It will be understood that the fluorescence in the indirect fluorescein-labeled antibody test is a bright apple-green which appears as a dark spot in the following photographs.

FIG. 1 is a photograph of a culture HeLa-cell following peroxidase staining with the indirect peroxidase-labeled antibody test. Dense deposits of reaction are present at the level of the nuclear membrane and a discrete reaction is seen in the plasma membrane. FIG. 1 is a photograph at 2200 magnification.

Figure 2:

FIG. 2 is a photograph of a cultured mast cell tumor magnified 2,200 times. The peroxidase staining was produced by the indirect peroxidase-labeled antibody test of this invention. A dense layer of reaction product is noted in the periphery of the cells and in discrete cytoplasmic granules.

Figure 3:
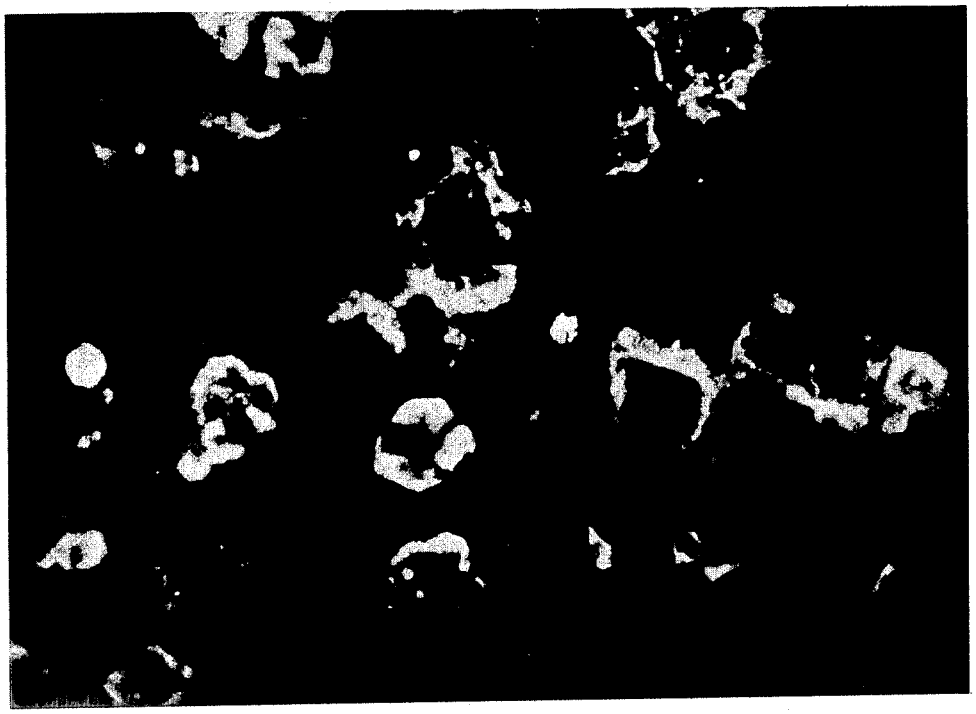

FIG. 3 is a frozen section of the spleen showing Rauscher Leukemia using the fluorescein-labeled antibody test. Intense reaction is seen at the plasma membrane level. The neoplastic cells are easily and clearly identified against the dark background of normal cells.

Figure 4:

FIG. 4 is a transplantable mammary tumor labeled with fluorscein by the indirect fluorscein-labeled test. The metastases are demonstrated in a frozen section of liver which are easily identified against the dark background of normal cells. The magnification is 500.

Figure 5:
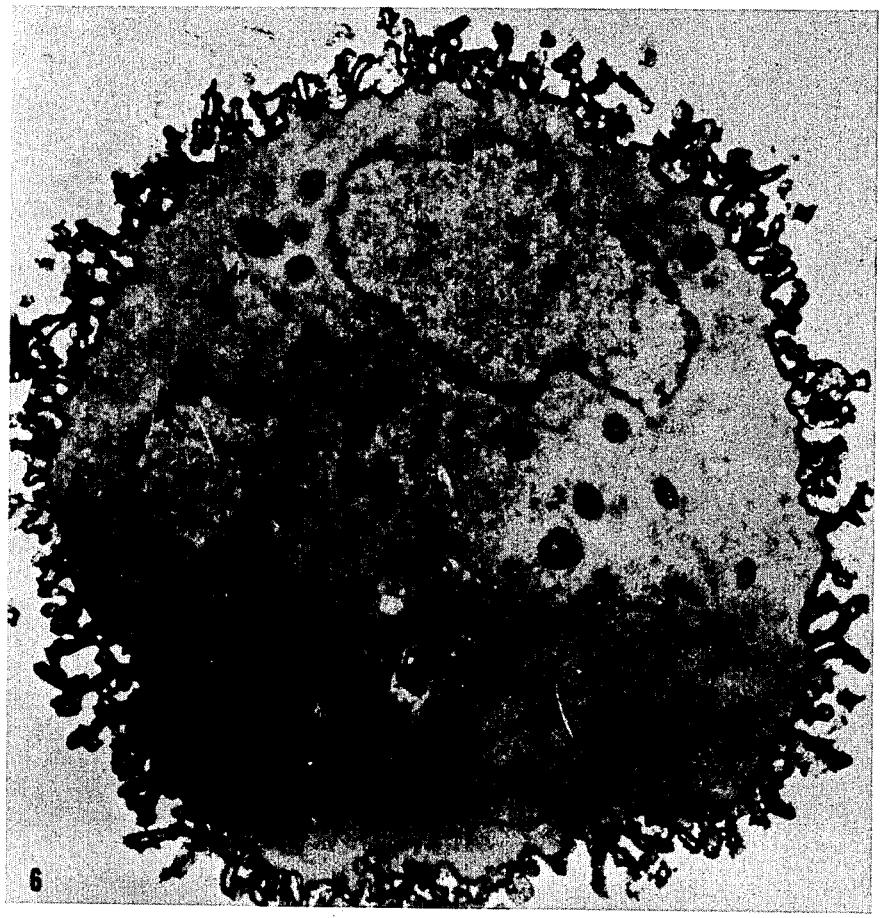

FIG. 5 is a mastocytoma cell magnified 17,000 times. The peroxidase staining resulted from the indirect peroxidase-labeled antibody test described above. Strong immunostaining for the beta-subunit of human chorionic gonadotropin is seen in the plasma membrane.

Figure 6:

FIG. 6 is a greater magnification of the mastocytoma cell shown in FIG. 5 displaying dense zones of electron-opaque reactive product indicating the presence of high concentrations of human chorionic gonadotropin at the level of the plasma membrane. FIG. 6 is a 65,00 magnification.

The tissue culture cells used in this investigation were obtained from Flow Laboratories, Rockville, Md., The Americal Type Culture Collection Cell Repository, Rockville, Maryland and from the Cancer Research Laboratories of the Allegheny General Hospital. The HeLa-cell for example, was obtained from the Americal Type Culture Collection. The cell line used was cultured in 250 ml plastic Falcon flasks and propigated at 37 C in Eagle's minimum essential medium with Earle's salts and ten percent fetal bovine serum, glutamine and gentamicin. The mastocytoma cells were obtained from the fluid of a ascites tumor in mice seven days after intraperitoneal enoculation of one million cells. The mammary andenocarcinoma, a malignant neoplasms originally induced with 7,12-dimethyldenzanthrazene (1,2) was obtained by excision of the neoplasm 14 days after its transplant in female Fisher syngeneic rats. These neoplasms have been described by way of example and the further malignant neoplasms are set forth in Tables I and II.

The diagnostic cell test of this invention is believed to be the first clinical procedure which can establish the absence of human chorionic gonadotropin in a cell speciman or culture. The combination of these highly specific and sensitive techniques have now established that human chorionic gonadotropin is a common denominator of all cells catagorized as cancer. Therefore, the absence of hCG in a cell culture or cell mass establishes the absence of cancer.

TABLE I

IN VIVO, EXPERIMENTAL ANIMAL NEOPLASMS

1. P-815-X2, murine mastocytoma, DBA/J2 mouse
   (a) Solid neoplasm
   (b) Liver metastases (c) Lung metastases
(d) Ascites tumor
2. Rauscher Leukemia, SJSL mouse
    (a) Spleen
    (b) Liver
3. Lewis Lung Carcinoma, Subline LL12B46,BDF1 mouse
    (a) Lung
    (b) Liver metastases
4. T1699 Transplantable Mammary Neoplasm, DBA/J2 mouse
    (a) Mammary neoplasm
    (b) Liver metastases
5. Mouse spontaneous mammary neoplasm, C3H/HeJ mouse
    (a) mammary neoplasm
6. Sarcoma-180, adult swiss albino female mouse
    (a) Ascites tumor
7. 13762 Transplantable mammary neoplasm, Fischer 344 CRBL rat (6)
    (a) Mammary neoplasm
8. SA-7 Virus Induced hamster neoplasm
9. SV-40 Virus Induced hampster neoplasm
10. CCRF S-180 II Sarcoma 180, murine

TABLE II

HUMAN MATERIAL

Malignant Neoplasms—Tested Positive

1. Malignant meningioma
2. Squamous cell carsodoma of lung.
3. Adenocarcinoma of lung
4. Adenocarcinoma of breast
5. Malignant Lymphoma (not-Hodgkins)
6. Ovarian carcinoma-undifferentiated
7. Testicular seminoma
8. Adenocarcinoma of colon
9. HeLa: Squamous cell carcinoma of cervix
10. HEp-2: Squamous cell carcinoma of Larynx
11. Detroit 562: Carcinoma of pharynx Controls-Benign Neoplasms—Tested Negative 1. Benign teratoma (dermoid cyst)
2. Prostatic hyperplasia Normal Cell Cultures—Tested Negative

| CELL LINE | ORGAN OF ORIGIN |
| --- | --- |
| 1. Girardi CCL-27 | Human adult heart |
| 2. Chang Liver | Human adult Liver |
| 3. MA-196 | Human adult skin & muscle |
| 4. MA-409 | Human adult cornea |
| 5. WI-38 | Human diploid fibroblast embryonic lung |
| 6. FLOW-4000 | Human embryonic kidney |

We claim:
1. A diagnostic test kit for detecting the absence or the presence of suspected malignant neoplastic cells in a cell specimen by testing for human chorionic gonadotropin, said diagnostic cell test kit comprising:
    (a) antiserum specific to the beta-subunit of human chorionic gonadotropin, said beta-subunit having been raised in a host animal, for treating cell samples to be tested, followed by rinsing to remove any excess antiserum;
    (b) antiserum specific to gamma globulin of said host animal conjugated to fluorescein for adding to a portion of said sample to be tested which has been treated with said beta-subunit of human chorionic gonadotropin followed by examination of said portion with an ultraviolet microscope which passes the ultraviolet light through said cells; if fluorescein is found, the indirect fluorescein-labelled antibody test is considered positive; if no staining is found, this indirect test is considered negative; and
    (c) antiserum specific to said gamma globulin of said host animal conjugated to peroxidase for adding to a second portion of said cell specimen treated with said antiserum specific to the beta-subunit of human chorionic gonadotropin and peroxidase activator, added to said second cell sample followed by an examination of said second portion with a microscope to determine whether peroxidase staining has occurred, the indirect peroxidase-labelled antibody test is considered positive if staining is found; if no staining is found, the test is negative;
the cell test for human chorionic gonadotropin is then considered positive only if both indirect labelled antibody tests are positive; if both indirect antibody tests are negative or if one indirect labelled antibody test is positive and the other is negative, the diagnostic cell test is negative for human chorionic gonadotropin, establishing that neoplastic cells are not present in the cells tested.

* * * * *